United States Patent [19]
Montzka et al.

[11] 4,154,932
[45] May 15, 1979

[54] 6-OXAMORPHINANS

[75] Inventors: Thomas A. Montzka, Manlius; John D. Matiskella; Richard A. Partyka, both of Liverpool, all of N.Y.

[73] Assignee: Bristol-Myers Company, New York, N.Y.

[21] Appl. No.: 831,444

[22] Filed: Sep. 8, 1977

[51] Int. Cl.² ............................................. C07D 491/08
[52] U.S. Cl. ..................................... 546/63; 424/256; 546/97; 542/403
[58] Field of Search ...................... 260/293.55, 293.54, 260/DIG. 13

[56] References Cited
U.S. PATENT DOCUMENTS

| | | |
|---|---|---|
| 3,853,889 | 12/1974 | Monkovic et al. .............. 260/293.55 |
| 4,016,167 | 4/1977 | Montzka et al. ................ 260/293.55 |

*Primary Examiner*—Natalie Trousof
*Assistant Examiner*—Richard A. Schwartz
*Attorney, Agent, or Firm*—Richard R. Lloyd

[57] ABSTRACT

N-substituted 6-oxamorphinans have been found to possess potent analgetic, narcotic antagonist, antitussive, and ADH inhibitory activity. A particularly preferred compound is (−)-17-cyclopropylmethyl-3-hydroxy-6-oxamorphinan. The compounds are prepared by total synthesis and are not derived from opium alkaloids.

13 Claims, No Drawings

6-OXAMORPHINANS

SUMMARY OF THE INVENTION

6-Oxamorphinans of the formula

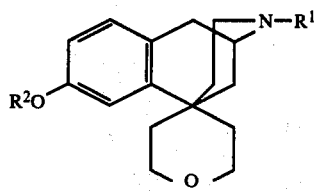

XXXV wherein R¹ is hydrogen, (lower)alkyl, cyclopropylmethyl, cyclobutylmethyl, allyl, —CH₂C≡C—R³,

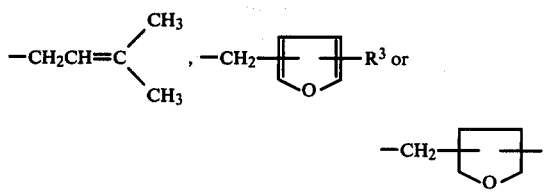

in which R³ is hydrogen or methyl, and R² is hydrogen, (lower)alkyl, (lower)alkanoyl or nicotinoyl, and pharmaceutically acceptable salts thereof, possess analgetic, narcotic antagonist, antitussive and/or ADH inhibitory activity, or are useful intermediates in the preparation of such compounds.

DESCRIPTION OF THE PRIOR ART

U.S. Pat. No. 3,853,889 discloses substituted 8-oxamorphinans having the formula

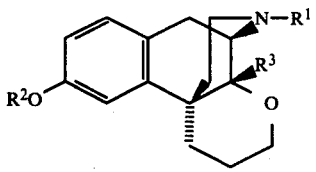

wherein R¹ is H, (lower)alkyl, (lower)alkenyl,

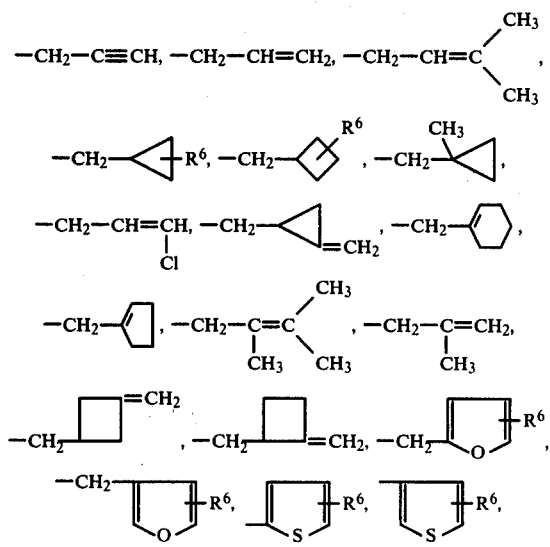

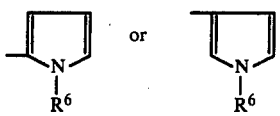

in which R⁶ is H or CH₃; R² is H, (lower)alkyl, (lower)alkanoyl, cinnamoyl,

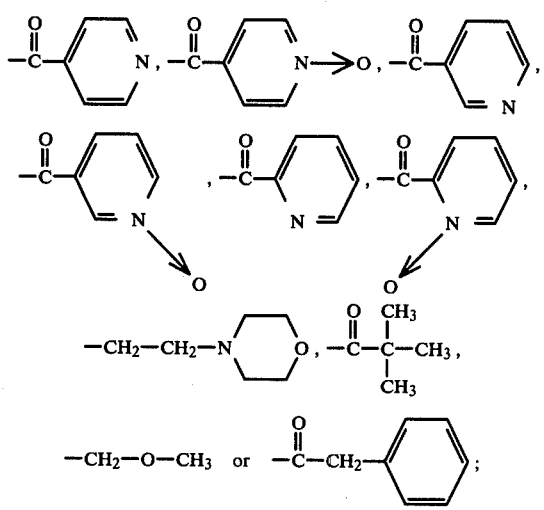

and R³ is H or (lower)alkyl; and pharmaceutically acceptable acid addition salts thereof. The compounds are stated to be analgetic agents, narcotic antagonists or intermediates in the preparation of such agents. U.S. Pat. No. 3,959,290, a continuation-in-part of the above-identified patent, has a substantially identical disclosure.

U.S. Pat. No. 4,016,167 discloses substituted 6,8-dioxamorphinans having the formula

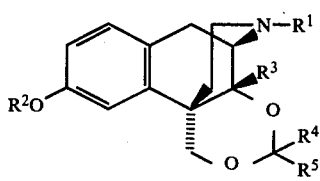

wherein R¹ is H, (lower)alkyl, (lower)alkenyl, —CH₂—C≡CH, —CH₂—CH=CH₂,

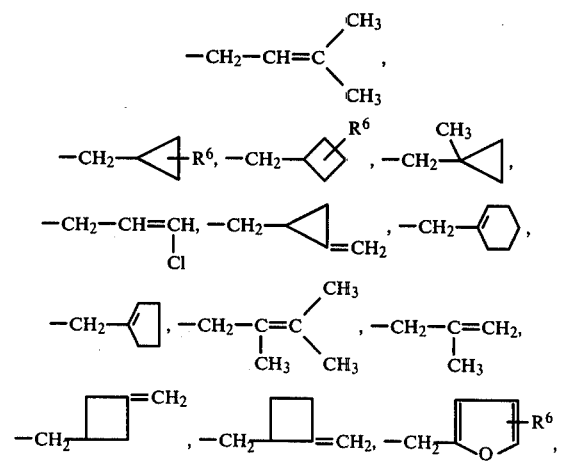

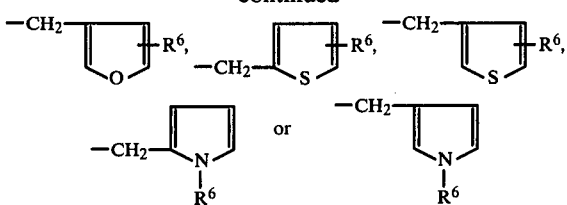

in which R⁶ is H or CH₃; R² is H, (lower)alkyl, (lower)alkanoyl, cinnamoyl,

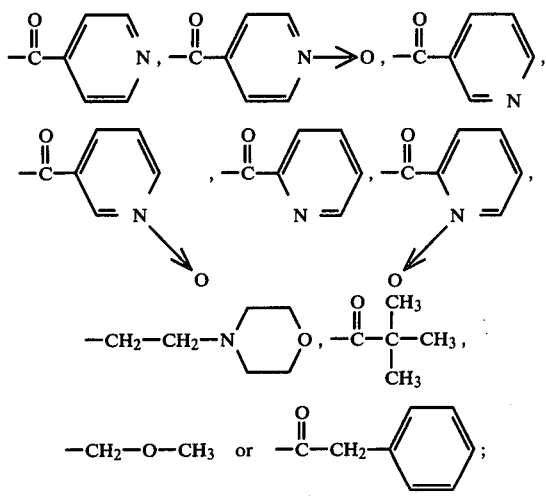

R³ is H or (lower)alkyl; and R⁴ and R⁵ are alike or different and each is H, (lower)alkyl or trifluoromethyl, or when taken together R⁴ and R⁵ are a carbonyl function or a spiroalkyl group of 3 to 7 carbon atoms; and pharmaceutically acceptable acid addition salts thereof. The compounds are stated to possess analgetic agonist-/antagonist activity or to be useful intermediates.

Complete Disclosure

This invention relates to 6-oxamorphinans of the formula

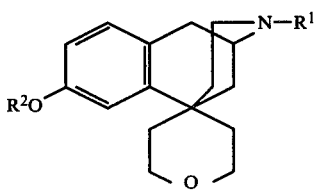 XXXV wherein R¹ is hydrogen, (lower)alkyl, cyclopropylmethyl, cyclobutylmethyl, allyl, —CH₂C≡C—R³,

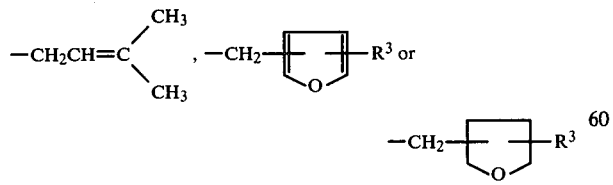

in which R³ is hydrogen or methyl, and R² is hydrogen, (lower)alkyl, (lower)alkanoyl or nicotinoyl, and pharmaceutically acceptable salts thereof, and to their total synthesis from the known compound, 6-carbomethoxy-8-methoxy-3-methyl-11-oxo-1,2,3,4,5,6-hexahydro-2,6-methano-3-benzazocine [5-carbomethoxy-2'-methoxy-2-methyl-9-oxo-6,7-benzomorphan].

Drug abuse by thrill-seeking youth or by people looking for an escape from the realities of everyday life has become more and more commonplace in our present society. One class of widely abused drugs are the narcotic analgetics such as codeine, morphine, meperidine, etc. It is because of the high addictive potential of these agents that much time and money are being expanded by the pharmaceutical industry and by governments to try and discover and develop new non-addicting analgetics and/or narcotic antagonists.

It was therefore an object of the present invention to find novel low abuse analgetics and/or narcotic antagonists. It was a further object of the present invention to develop a method of synthesis that would not be dependent upon opium alkaloids as starting materials.

The objects of the present invention have been achieved by the provision of the compounds of Formula XXXV and by their total synthesis from 6-carbomethoxy-8-methoxy-3-methyl-11-oxo-1,2,3,4,5,6-hexahydro-2,6-methano-3-benzazocine.

In a preferred embodiment of this invention the compounds have the structure of Formula XXXV in which R¹ is hydrogen, (lower)alkyl, cyclopropylmethyl or cyclobutylmethyl, and R² is hydrogen or (lower)alkyl, or a pharmaceutically acceptable salt thereof.

In a more preferred embodiment of this invention the compounds have the structure of Formula XXXV in which R¹ is hydrogen, methyl, cyclopropylmethyl or cyclobutylmethyl, and R² is hydrogen or methyl, or a pharmaceutically acceptable salt thereof.

In a still more preferred embodiment of this invention the compounds have the structure of Formula XXXV in which R¹ is cyclopropylmethyl and R² is hydrogen or methyl, or a pharmaceutically acceptable salt thereof.

In another still more preferred embodiment of this invention the compounds have the structure of Formula XXXV in which R¹ is cyclobutylmethyl and R² is hydrogen or methyl, or a pharmaceutically acceptable salt thereof.

A most preferred embodiment is the compound of Formula XXXV in which R¹ is cyclopropylmethyl and R² is hydrogen (and most preferably the (−)-isomer of said compound), or a pharmaceutically acceptable salt thereof.

Another most preferred embodiment is the compound of Formula XXXV in which R¹ is cyclobutylmethyl and R² is hydrogen (and most preferably the (−)-isomer of said compound), or a pharmaceutically acceptable salt thereof.

Another most preferred embodiment is the compound of Formula XXXV in which R¹ is cyclopropylmethyl and R² is methyl (and most preferably the (−)-isomer of said compound), or a pharmaceutically acceptable salt thereof.

The compounds of the present invention have the 6-oxamorphinan nucleus which is numbered and represented by the following plane formula.

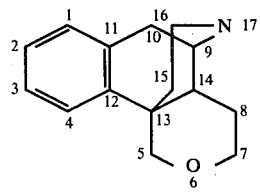

Although the preceding nucleus and the structure of Formula XXXV above have been drawn in planar form, the 6-oxamorphinans are optically active compounds and may exist as the racemic (±) mixture or as the individual (+) and (−) isomers. The optical isomers of the compounds of Formula XXXV can be graphically illustrated as follows:

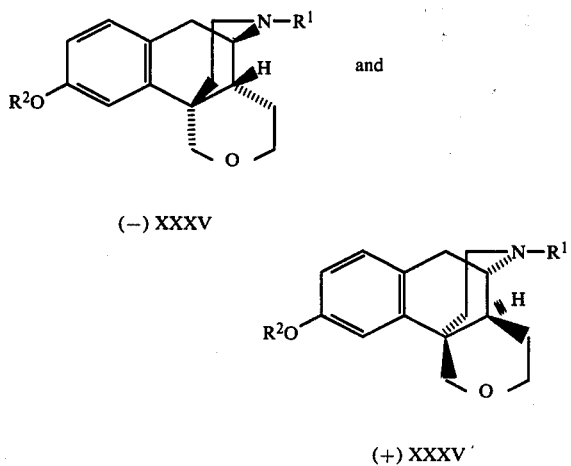

For convenience, planar formulae will normally be used throughout the specification and claims. It is to be understood, however, that such planar formulae or the use of the designation "6-oxamorphinan" is meant to include the racemic mixture and the individual (+) and (−) isomers unless the specific text indicates otherwise.

For the purpose of this disclosure and the appended claims, the term (lower)alkyl is defined as a straight or branched chain alkyl group containing from 1 to 6 carbon atoms, e.g. methyl, propyl, isobutyl, etc. The term (lower)alkanoyl is defined as a straight or branched chain alkanoyl radical containing from 2 to 6 carbon atoms, e.g. acetyl, propionyl, isobutyryl, etc. The term pharmaceutically acceptable salt is defined as a salt of a compound of this invention with any of the inorganic or organic acids which are commonly used to produce nontoxic salts of medicinal agents containing amine functions. Illustrative examples would be those salts formed by mixing the compounds of Formula XXX with hydrochloric, sulfuric, nitric, phosphoric, phosphorous, hydrobromic, maleic, malic, ascorbic, citric, tartaric, pamoic, lauric, stearic, palmitic, oleic, myristic, lauryl sulfuric, naphthalenesulfonic, linoleic or linolenic acid, or the like.

The compounds of this invention are prepared by a total synthesis comprising multiple steps, as outlined in the following chart.

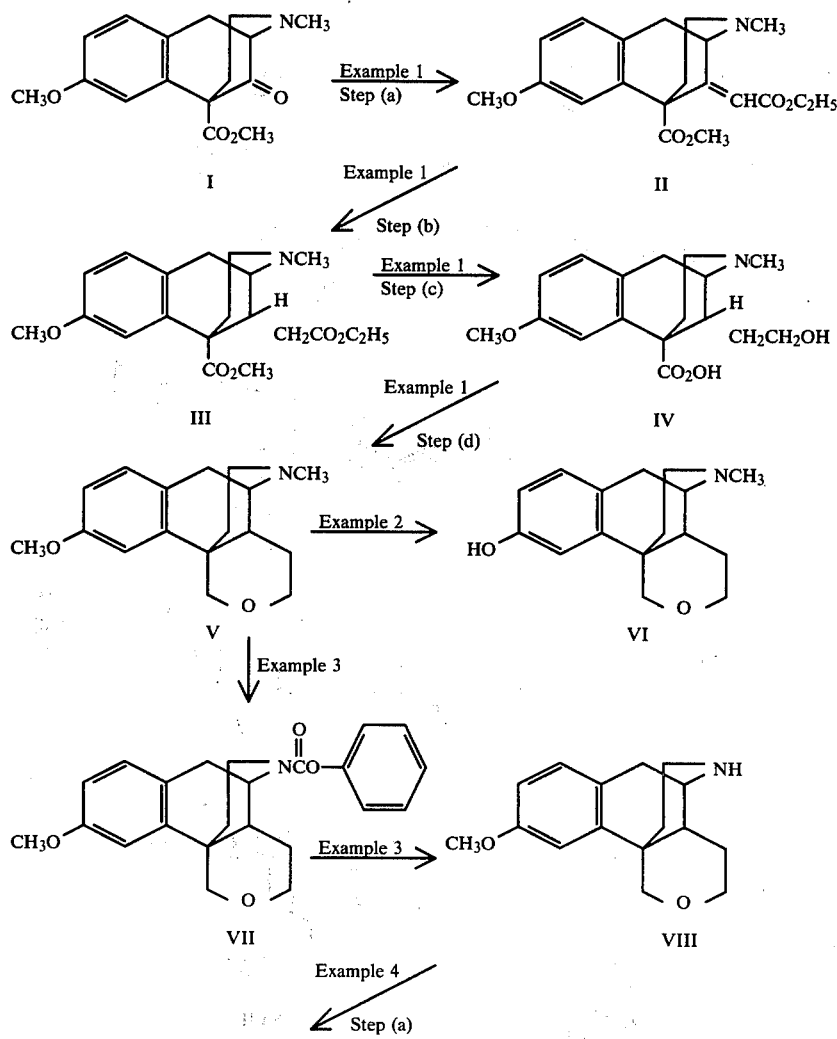

-continued
Chart I
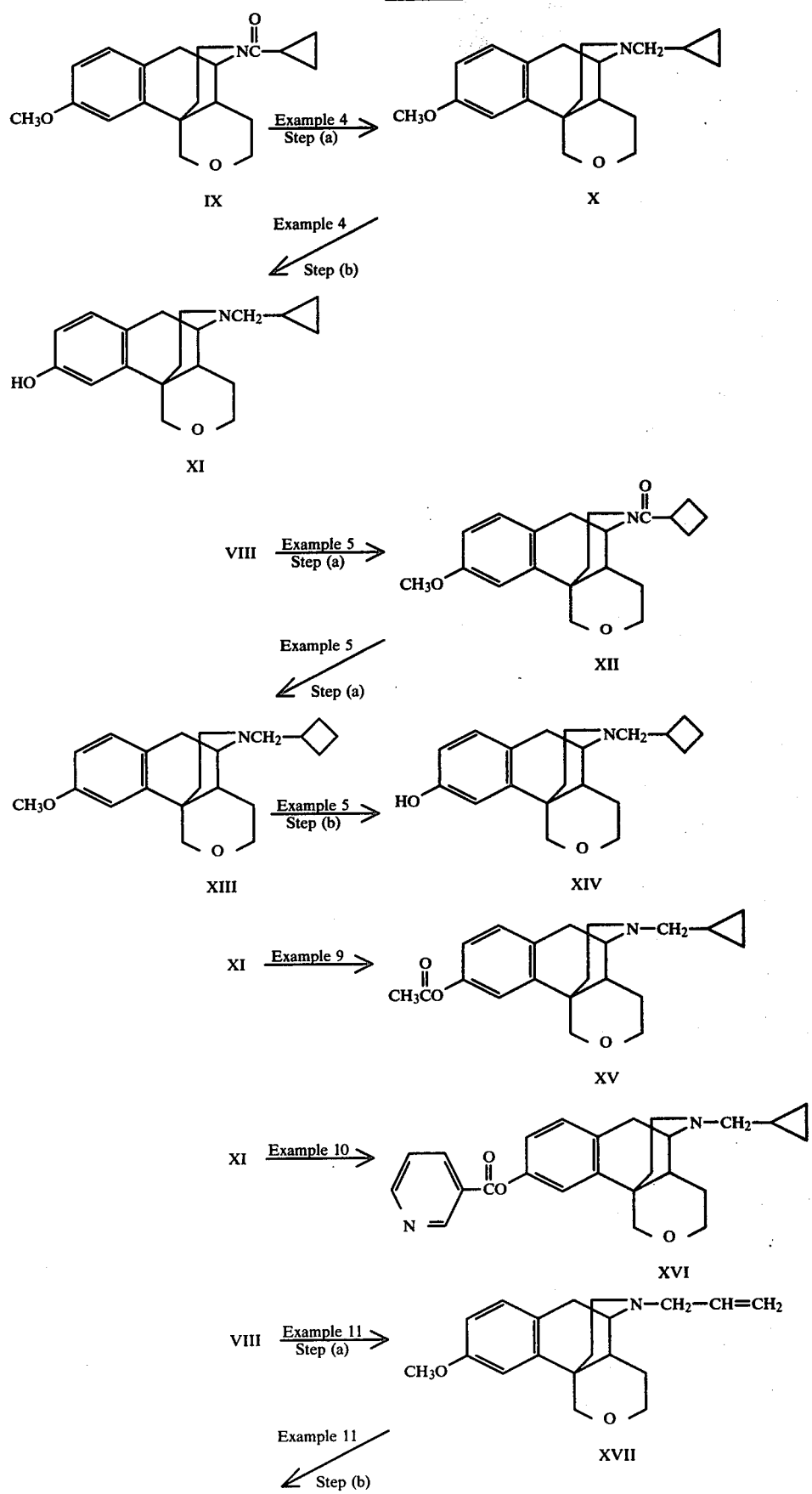

-continued
Chart I
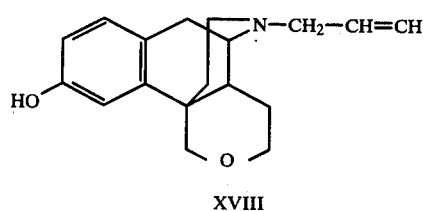
XVIII
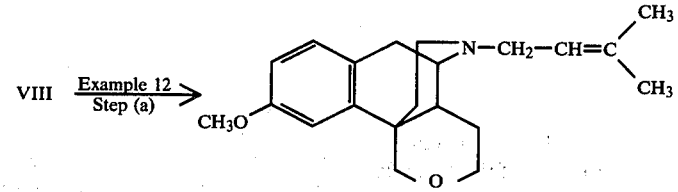
XIX
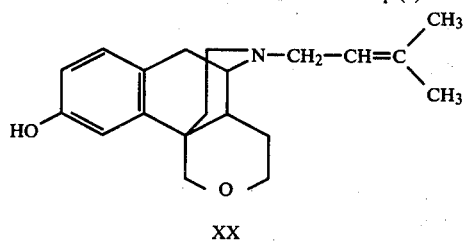
XX
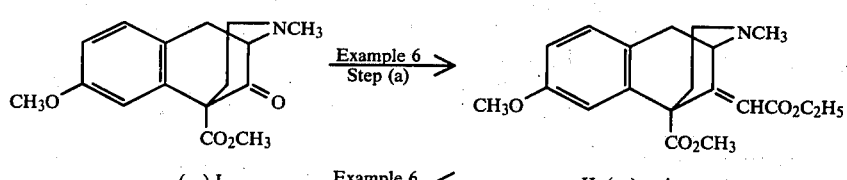
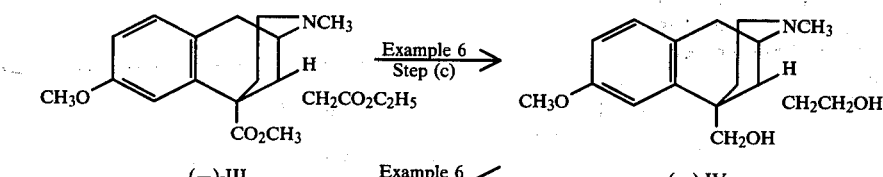
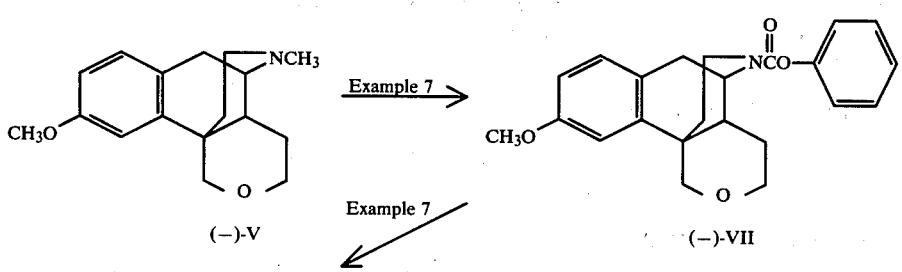
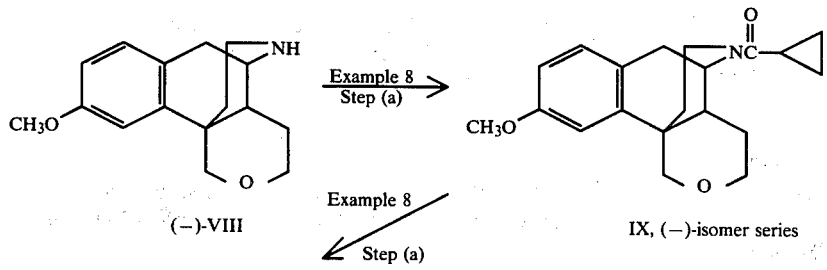

-continued
Chart I

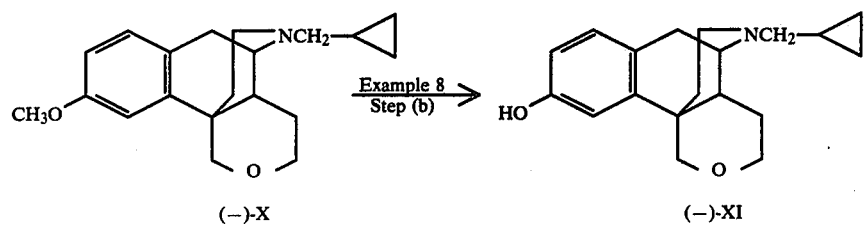

(−)-X        (−)-XI

In another aspect, this invention relates to a process for the preparation of a 6-oxamorphinan of the formula

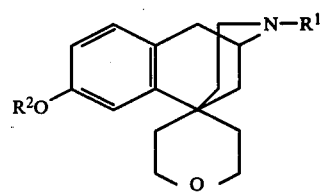 XXXV wherein $R^1$ is (lower)alkyl, cyclopropylmethyl, cyclobutylmethyl, allyl, —CH$_2$C≡C—R$^3$,

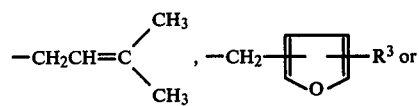

in which $R^3$ is hydrogen or methyl, $R^2$ is hydrogen, (lower)alkyl, (lower)alkanoyl or nicotinoyl, or a pharmaceutically acceptable salt thereof, which process comprises the consecutive steps of (A) treating a compound of the formula

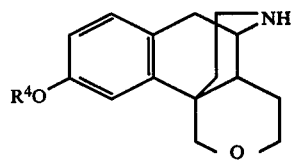 XXI in which $R^4$ is (lower)alkyl with an alkylating or acylating agent of the formula

X—(X)—W in which W is hydrogen, (lower)alkyl, cyclopropyl, cyclobutyl,

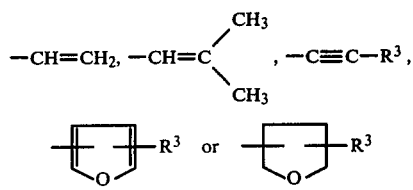

in which $R^3$ is hydrogen or methyl, Z is

and x is chloro, bromo or iodo, in an inert organic solvent, in the presence of an appropriate base, to produce a compound having the formula

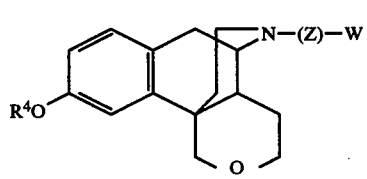 XXII in which $R^4$, Z and W are as defined above; and when Z is a carbonyl moiety (B) treating compound XXII with a reducing agent selected from lithium aluminum hydride, aluminum hydride, diborane and sodium bis(2-methoxyethoxy)aluminum hydride, in an inert organic solvent, to produce a compound having the formula

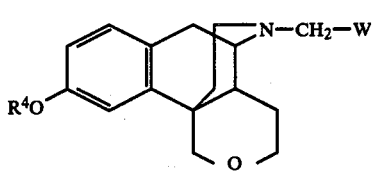 XXIII in which $R^4$ and W are as defined above; and when desired (C) cleaving the ether function of compound XXII or XXIII with sodium thioethoxide, hydrobomic acid, boron trifluoride or pyridine hydrochloride, in an inert inorganic solvent, to produce a compound having the formula

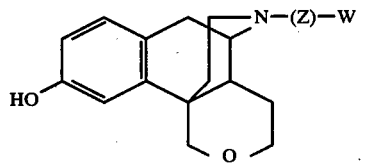 XXIV in which Z and W are as defined above; and if desired (D) acylating compound XXIV with an acylating derivative of an acid of the formula

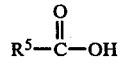

in which $R^5$ is (lower)alkyl or 3-pyridyl, in an inert organic solvent, to produce a compound of the formula

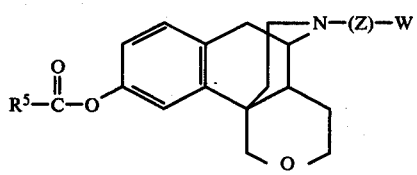

in which $R^5$, Z and W are as defined above.

XXI in which $R^4$ is methyl), for use as the starting material in the above process. Compounds of Formula XXI in which $R^4$ is (lower)alkyl other than methyl may be prepared from Compound VI of Chart I by the following reaction scheme which illustrates the preparation of the corresponding ethoxy compound. The corresponding propoxy, butoxy, etc. compounds may be prepared in a similar manner by utilizing the appropriate alkyl halide, e.g. propyl iodide or butyl iodide.

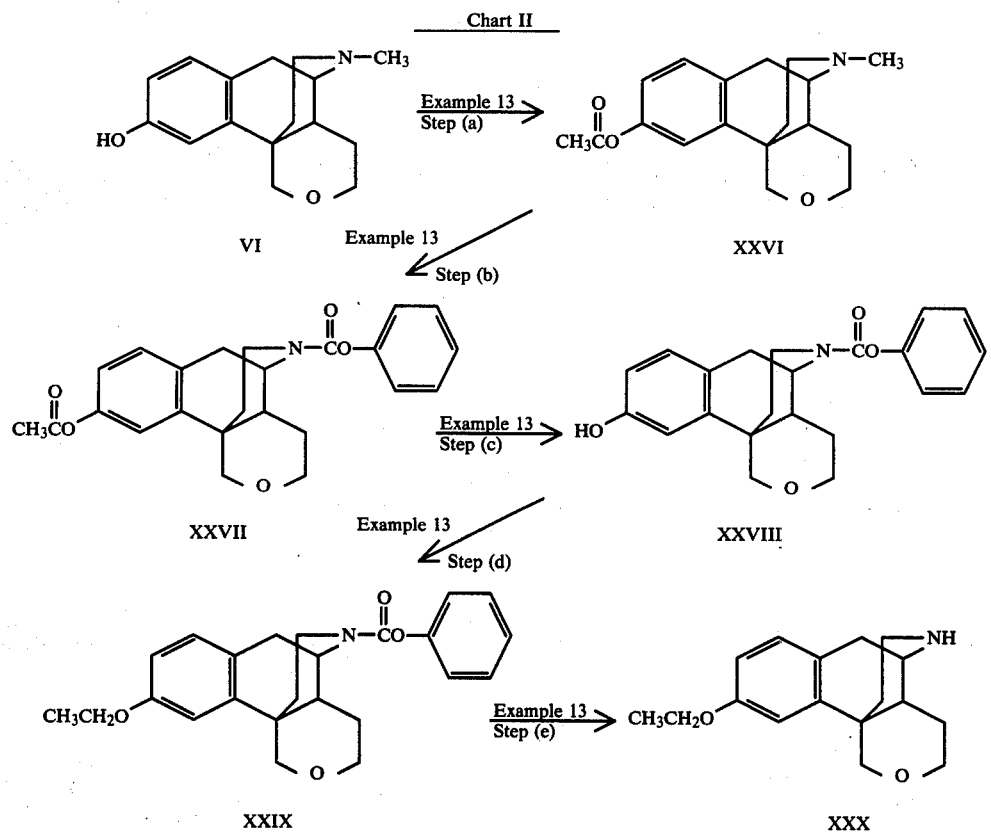

In starting material XXI for the above process, $R^4$ may be (lower)alkyl. In Chart I above the initial starting material (I) contains a methoxy group in the corresponding position and thus produces the compound of Formula VIII, which also contains a methoxy group in the corresponding position (i.e. a compound of Formula Alternatively, products of Formula XXXV in which $R^2$ is (lower)alkoxy other than methoxy may be prepared from the compound of Formula VIII by the following reaction scheme which illustrates the preparation of the compound of Formula XXXV in which $R^1$ is cyclopropylmethyl and $R^2$ is ethoxy.

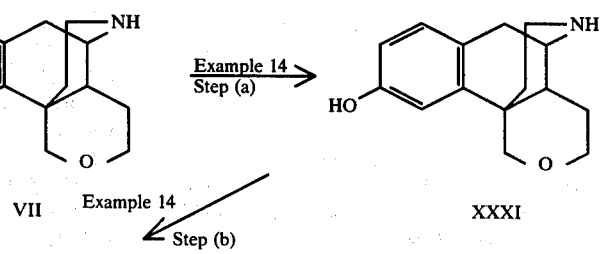

-continued
Chart III

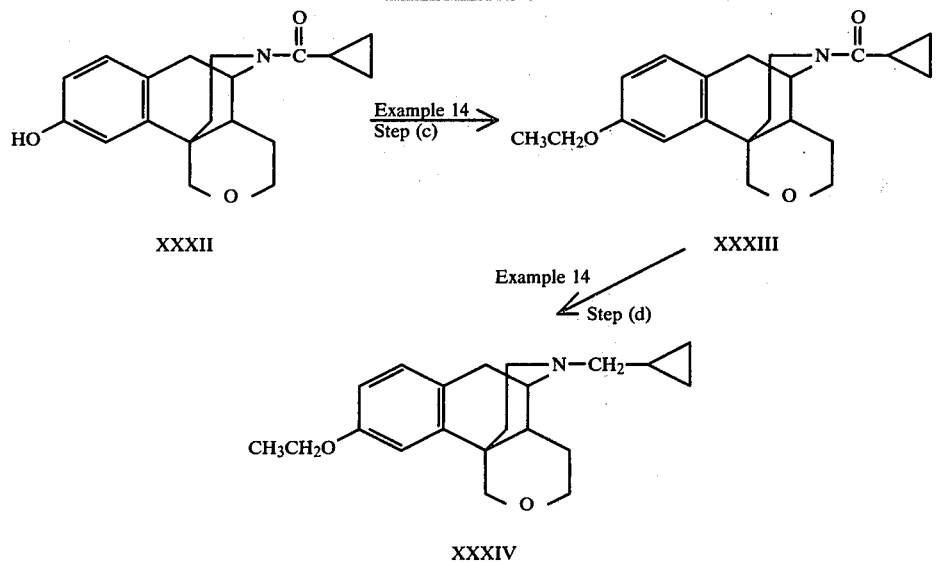

For the purpose of this disclosure the term "inert organic solvent" means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower-)alkanols such as methanol, ethanol, n-propanol, isopropanol and the like.

The term "appropriate base" includes inorganic salts such as NaOH, KOH, $K_2CO_3$, $Na_2CO_3$, $NaHCO_3$, $KHCO_3$, and the like and those tertiary amines commonly employed as a proton acceptor in acylation reactions. Such amines are tri(lower)alkylamines, e.g. trimethylamine, triethylamine, and the like, pyridine, dimethylaniline, N-methylpiperidine, and the like.

Acceptable inert organic solvents for use in the reduction step (B) in the above process include among others, diethyl ether, dioxane, tetrahydrofuran, benzene, xylene, toluene and the like.

All of the compounds of this invention are novel and valuable for their properties as analgetic and/or narcotic antagonist agents, or as intermediates in the preparation of compounds having these biological properties. Some of these compounds also possess potent antitussive or ADH (anti diuretic hormone) inhibitory activity.

It is well known in the narcotic analgestic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

In vivo testing was conducted on many of the compounds of the present invention. Table 1 reports the number of mgs per kg of body weight which were required to produce an agonist or antagonist effect in 50% of the mice tested ($ED_{50}$).

Table 1

| Test Compound | $ED_{50}$ (mg/kg, s.c.) 95% confidence limits | |
|---|---|---|
| | Agonist Activity Phenylquinone Writhing[1] | Antagonist Activity Oxymorphone Straub Tail[2] |
| (±)–V | 1.32 | >20 |
| (±)–VI | 0.34 | >40 |
| (±)–VIII | ~40 | >40 |
| (±)–X | 0.38 | 10 |
| (±)–XI | 0.037 | 0.76 |
| (±)–XIII | 0.38 | ~15 |
| (±)–XIV | 0.015 | ~6 |
| (−)–X | 0.14 | ~6 |
| (−)–XI | 0.028 | 0.44 |

[1] A 50% reduction in number of phenylquinone induced writhings [Siegmund, E.A. et al., Proc. Soc. Biol. & Med., 95, 729, (1957)].
[2] Antagonism of Straub Tail induced by oxymorphone (2 mg/kg, s.c.) in 50% of the mice.

In more detailed tests, a preferred compound of this invention, (−)-17-cyclopropylmethyl-3-hydroxy-6-oxamorphinan [(−)-XI], was compared with buprenorphine, butorphanol and morphine sulfate for analgetic and antitussive activity, and with buprenorphine, butorphanol and naloxone for antagonist activity.

Table 2 shows that the analgetic potencies of all three antagonist analgetics were approximately equal by the subcutaneous route of administration, whereas the oral potency of (−)-XI was markedly better than butorphanol and equivalent to buprenorphine. The oral/parenteral analgetic potency ratio for (−)-XI was comparable to buprenorphine and approximately ten times better than butorphanol. The parenteral/intraventricular potency ratios indicate that (−)-XI and butorphanol penetrate the blood-brain barrier more readily than either morphine or buprenorphine and to about the same degree as each other.

Table 3 shows that (−)-XI is about twice as potent as butorphanol in blocking the effects of the opioids, oxymorphone and morphine. A comparison of the oral/parenteral potency ratios relative to antagonist activity also shows that the oral/parenteral ratio of (−)-XI is superior to butorphanol and about equal to that of buprenorphine. The very poor oral/parenteral potency ratios for naloxone agree with its relative lack of oral activity in man except at exceptionally high doses.

Table 2

ANALGETIC ACTIVITY
ED$_{50}$ - mg/kg (95% Confidence Limits)

| Compound | Mouse Writhing sc | po | po/sc | Rat Writhing sc | po | po/sc | Rat Vocalization sc | po | po/sc |
|---|---|---|---|---|---|---|---|---|---|
| (−)−XI | 0.028 | 0.30 | 11 | 0.021 | 0.22 | 11 | 0.006 | 0.11 | 18 |
| Buprenorphine | 0.021 | 0.27 | 13 | 0.013 | 0.16 | 12 | 0.005 | ~0.08 | ~16 |
| Butorphanol | 0.045 | 5.1 | 113 | 0.040 | 2.1 | 53 | 0.012 | 0.83 | 69 |
| Morphine SO$_4$ | 0.26 | 3.1 | 12 | 0.16 | 1.6 | 10 | 0.19 | 2.1 | 11 |

| Compound | Intraventricular | sc/I. Vent. |
|---|---|---|
| (−)−XI | 0.0012 | 23 |
| Buprenorphine | 0.0004 | 53 |
| Butorphanol | 0.0019 | 24 |
| Morphine SO$_4$ | 0.0032 | 81 |

Table 3

ANTAGONIST ACTIVITY
ED$_{50}$ - mg/kg (95% Confidence Limits)

| Compound | Oxymorphone-Induced Straub Tail sc | po | po/sc | Morphine Antagonism Rat Tail Flick sc | po | po/sc |
|---|---|---|---|---|---|---|
| (−)-XI | 0.44 | 14 | 32 | 0.26 | ~3 | 12 |
| Butorphanol | 0.98 | 55 | 56 | 0.43 | 22 | 51 |
| Buprenorphine | 0.46 | N.D. | — | 0.063 | 0.92 | 15 |
| Naloxone | 0.09 | 13 | 144 | 0.010 | 2.7 | 270 |

Table 4 shows that (−)-XI is a potent antitussive agent in the unanesthetized dog following subcutaneous administration. Its ED$_{50}$ indicates that it is 1.7 times as potent as butorphanol and approximately 7 times as potent as morphine sulfate by the subcutaneous route. Further, the compound appears to have a significantly longer duration of activity than either butorphanol or morphine sulfate.

Table 4

Comparative Antitussive Effects of (−)−XI, Butorphanol and Morphine Sulfate in the Unanesthetized Dog

| Compound and Dose (mg/kg sc) | N | Percent Inhibition of Cough Response | | | | | | |
|---|---|---|---|---|---|---|---|---|
| | | 15 | 30 | 60 | 120 | 180 | 240 | 300 min |
| Butorphanol[1] 0.1 | 5 | 98 | 96 | 92 | 84 | 64 | 41 | 28 |
| Morphine SO$_4$[2] 0.1 | 6 | 52 | 70 | 86 | 67 | 41 | 41 | 32 |
| (−)−XI[3] 0.05 | 1 | 100 | 100 | 100 | 100 | 100 | 100 | 100 |
| (−)−XI 0.02 | 3 | 90 | 99 | 88 | 70 | 67 | 67 | 64 |
| (−)−XI 0.01 | 2 | 38 | 68 | 86 | 98 | 62 | 50 | 24 |
| (−)−XI 0.005 | 1 | 7 | 52 | 15 | 41 | 41 | 37 | 33 |

[1]ED$_{50}$ = 0.01 mg/kg sc;
[2]ED$_{50}$ = 0.04 mg/kg sc;
[3]ED$_{50}$ = 0.006 mg/kg sc

The oral antitussive ED$_{50}$'s in the unanesthetized dog for the above three compounds have been determined to be as follows:

| Butorphanol | ED$_{50}$ = 0.32 mg/kg po |
|---|---|
| Morphine Sulfate | ED$_{50}$ = 0.62 mg/kg po |
| (−)−XI | ED$_{50}$ = 0.04 mg/kg po |

These values indicate that (−)-XI is 8 times as potent as butorphanol and 16 times as potent as morphine sulfate by the oral route.

Buprenorphine and (−)XI were tested for physical dependence liability in mice. In primary physical dependence tests, mice treated for two days with repeated subcutaneous injections of either (−)-XI or buprenorphine did not exhibit withdrawal jumping (abstinence) when challenged with naloxone. Thus, neither compound showed any physical dependence liability in this test model. The compounds were then tested as substitutes for morphine in withdrawn morphine-dependent mice. Compound (−)-XI showed no evidence of substitution for morphine at doses of from 3 to 54 mg/kg sc. However, complete substitution for morphine was shown by buprenorphine at doses of 1 mg/kg sc, or less. On the basis of this test model, it is predicted that the physical dependence liability of (−)-XI in man will be nil or of a low order. However, the animal data indicate that buprenorphine will be morphine-like in man.

The following examples are intended to illustrate the invention without limiting it in any way.

EXAMPLE 1

3-Methoxy-17-methyl-6-oxamorphinan (V)

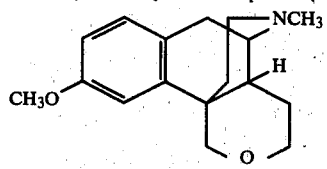

(a)
11-Carbethoxymethylidine-6-carbomethoxy-8-methoxy-3-methyl-1,2,3,4,5,6-hexahydro-2,6-methano-3-benzazocine (II)

A solution of triethyl phosphonoacetate (9 g; 0.04 m) in benzene (50 ml.) was slowly added to a suspension of NaH (1.92 g of a 50% dispersion in mineral oil; 0.04 m) in benzene (50 ml.) and the mixture was stirred for 45 minutes. A solution of 6-carbomethoxy-8-methoxy-3-methyl-11-oxo-1,2,3,4,5,6-hexahydro-2,6-methano-3-benzazocine [(I), prepared by the procedure of Example 5 of U.S. Pat. No. 4,016,167] (11.6 g; 0.04 m) in benzene (50 ml.) was added and the mixture was stirred in an oil bath at 45° C. for 3 hours. The mixture was allowed to cool overnight (18 hours) and then diluted with water (100 ml.). The benezene layer was separated, washed with saturated NaCl solution, dried (MgSO$_4$), filtered, and concentrated. The residue was taken up in acetonitrile, washed with n-pentane and concentrated to give an oil (14 g). GLC analysis indicated this material to contain about 88% of a mixture of isomers of the title compound.

(b) 11α-Carbethoxymethyl-6-carbomethoxy-8-methoxy-3-methyl-1,2,3,4,5,6-hexahydro-2,6-methano-3-benzazocine (III)

The crude material (II) prepared in step (a) (14 g) was taken up in 200 ml. ethanol and hydrogenated at 45 psi using 3.5 g 10% palladium on carbon as catalyst until the theoretical hydrogen uptake was observed (~40 hours). The catalyst was removed by filtration and the filtrate was concentrated to leave crystalline material. This material was recrystallized from ethanol-water to give the pure title compound (8 g); GLC analysis indicates >98% purity; mp 117°-118° C.

Anal. Calc'd for $C_{20}H_{27}NO_5$: C, 66.46; H, 7.53; N, 3.88. Found: C, 66.17, H, 7.38; N, 3.98.

(c) 11α-(2'-Hydroxyethyl)-6-hydroxymethyl-8-methoxy-3-methyl-1,2,3,4,5,6-hexahydro-2,6-methano-3-benzazocine (IV)

A solution of the product (III) of step (b) (4.1 g; 0.0114 m) in tetrahydrofuran was added to a suspension of LiAlH₄ (1.7 g) in tetrahydrofuran (100 ml.). This mixture was heated at reflux for 19 hours. After cooling, this mixture was cautiously treated with 5 ml. saturated aqueous $Na_2SO_4$ solution and warmed with stirring until the solids were white. The solids were removed by filtration and the filtrate was concentrated. The crystalline residue was recrystallized from acetone-methanol (10:1) to give the title compound, mp 161°-162° C.

Anal. Calc'd for $C_{17}H_{25}NO_3$: C, 70.07; H, 8.65; N, 4.81. Found: C, 70.43; H, 8.76; N, 4.64.

(d) 3-Methoxy-17-methyl-6-oxamorphinan (V)

Material (IV) prepared in step (c) (11.6 g; 0.04 m) was treated with 100 ml. 10N sulfuric acid and heated 4 hours on a steam bath. This solution was cooled in an ice bath, basified with concentrated ammonium hydroxide and extracted with methylene chloride. The extracts were dried (MgSO₄), filtered, and concentrated. GLC on the resulting oil indicated incomplete reaction. The above procedure was repeated to give an oil (9.8 g) which GLC indicated ~99% pure. The oil was converted to a hydrochloride salt in 2-propanol, mp 255°-260° C. (decomp).

Anal. Calc'd for $C_{17}H_{23}NO_2 \cdot HCl$: C, 65.91; H, 7.80; N, 4.53. Found: C, 65.57; H, 7.83; N, 4.39.

EXAMPLE 2

3-Hydroxy-17-methyl-6-oxamorphinan (VI)

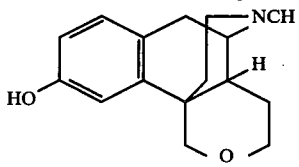

VI

A mixture of the product (V) of Example 1, step (d) (0.002 m) and sodium thioethoxide (0.03 m) (prepared from sodium hydride and ethyl mercaptan) in 30 ml. dimethylformamide was heated at reflux under nitrogen for 3 hours. The solvent was removed at reduced pressure. The cooled residue was treated with water, acidified with acetic acid, then basified with potassium carbonate and extracted with methylene chloride. The extracts were dried (Na₂SO₄), filtered, and concentrated. The residue was crystallized from acetonitrile then converted to a fumarate salt in 1-propanol (3/4 fumaric acid per mole of base as indicated by nmr and analysis), mp 213°-223° C. (decomp).

Anal. Calc'd for $C_{16}H_{21}NO_2 \cdot 3/4 (C_4H_4O_4)$: C, 65.87; H, 6.99; N, 4.05. Found: C, 65.36; H, 7.22; N, 3.84; H₂O, 0.76.

EXAMPLE 3

3-Methoxy-6-oxamorphinan (VIII)

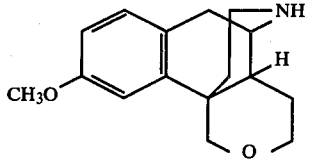

VIII

A refluxing mixture of the product (V) of Example 1, step (d) (0.029 m obtained from 8.9 g of the hydrochloride salt) and 10 g potassium carbonate in toluene (100 ml.) was treated with a solution of phenyl chloroformate (13.5 g; 0.086 m) in toluene (50 ml.). This mixture was heated at reflux for 40 hours. The reaction mixture was cooled and treated with water. The layers were separated and the organic extract washed with saturated NaCl, dried (MgSO₄), filtered, and concentrated to give crude 17-carbophenoxy-3-methoxy-6-oxamorphinan (VII). This material was treated with a mixture of 400 ml. 2-propanol, 100 ml. water and 48 g potassium hydroxide and heated at reflux for 40 hours. The 2-propanol was removed at reduced pressure. The residue was diluted with water and extracted with methylene chloride. The extracts were dried (MgSO₄), filtered, and concentrated to give crude title product which was purified as a hydrogen fumarate salt from 1-propanol (9.8 g), mp 231°-233° C.

Anal. Calc'd for $C_{16}H_{21}NO_2 \cdot C_4H_4O_4$: C, 63.98; H, 6.71; N, 3.73. Found: C, 64.19, H, 6.94; N, 3.71.

EXAMPLE 4

17-Cyclopropylmethyl-3-hydroxy-6-oxamorphian (XI)

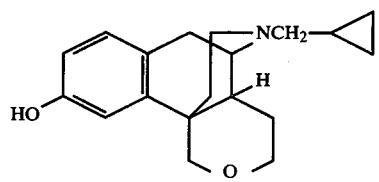

XI

(a) 17-Cyclopropylmethyl-3-methoxy-6-oxamorphinan (X)

A solution of the free base of the product (VIII) of Example 3 (0.005 m obtained from 1.9 g of the hydrogen fumarate salt) in methylene chloride (30 ml.) and triethylamine (1.5 ml.) was treated with a solution of cyclopropylcarbonyl chloride (0.58 g; 0.0055 m) in methylene chloride (5 ml.). After stirring for 2 hours this mixture was treated with dilute hydrochloric acid. The layers were separated and the methylene chloride layer was washed with water. The aqueous layers were extracted with two more portions of methylene chloride. The extracts were combined, dried (MgSO₄), filtered, and concentrated to give 17-cyclopropylcarbonyl-3-methoxy-6-oxamorphinan (IX) as an oil. This oil dissolved in tetrahydrofuran (20 ml.) was added to a suspension of lithium aluminum hydride (0.57 g) in tetrahydrofuran (20 ml.). This mixture was heated at reflux for 18 hours. To this cooled mixture was cautiously added saturated aqueous sodium sulfate solution (1.8 ml.) and a few drops of dilute sodium hydroxide. The reaction mixture was warmed until the solids were completely white. Solid sodium sulfate was added and the solids were removed by filtration and washed well with ethyl acetate. Concentration of the filtrates gave the title product (1.5 g) which was converted to a hydrochloride salt in ethanol (1.5 g), mp 259°–264° C.

Anal. Calc'd for $C_{20}H_{27}NO_2 \cdot HCl$: C, 68.66; H, 8.08; N, 4.01. Found: C, 68.38; H, 8.02; N, 4.02.

(b) 17-Cyclopropylmethyl-3-hydroxy-6-oxamorphinan (XI)

The product (X) of step (a) was demethylated to produce the title product using sodium thioethoxide in dimethylformamide by the general procedure described in Example 2. The resulting title product was converted to a hydrochloride salt in 2-propanol containing a few drops of water, mp 140° (decomposition of hydrate).

Anal. Calc'd for $C_{19}H_{25}NO_2 \cdot HCl \cdot \frac{1}{2}(H_2O)$: C, 66.17; H, 7.89; N, 4.06; $H_2O$, 2.55. Found: C, 66.00; H, 7.78; N, 4.01; $H_2O$, 2.83.

EXAMPLE 5

17-Cyclobutylmethyl-3-hydroxy-6-oxamorphinan (XIV)

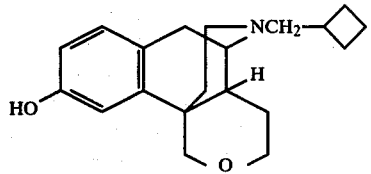

(a) 17-Cyclobutylmethyl-3-methoxy-6-oxamorphinan (XIII)

The general procedure of Example 4, step (a) was repeated, except that the cyclopropylcarbonyl chloride utilized therein was replaced by an equivalent amount of cyclobutylcarbonyl chloride. The title product was purified as the hydrochloride salt from ethanol, with mp 202°–206° C.

Anal. Calc'd for $C_{21}H_{29}NO_2 \cdot HCl$: C, 69.31; H, 8.31; N, 3.85. Found: C, 69.38; H, 8.56; N, 4.02.

(b) 17-Cyclobutylmethyl-3-hydroxy-6-oxamorphinan (XIV)

The product (XIII) of step (a) was demethylated to produce the title product using sodium thioethoxide in dimethylformamide by the general procedure described in Example 2. The title product was purified as a crystalline base from 95% ethanol; mp 197°–198° C.

Anal. Calc'd for $C_{20}H_{27}NO_2$: C, 76.64; H, 8.68; N, 4.47. Found: C, 76.60; H, 8.51; N, 4.51.

EXAMPLE 6

(-)-3-Methoxy-17-methyl-6-oxamorphinan [(-)-V]

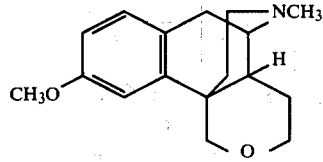

(a) 11-Carbethoxymethylidine-6-carbomethoxy-8-methoxy-3-methyl-1,2,3,4,5,6-hexahydro-2,6-methano-3-benzazocine [II, (−)-isomer series]

The general procedure of Example 1, step (a) was repeated, except that the racemic 6-carbomethoxy-8-methoxy-3-methyl-11-oxo-1,2,3,4,5,6-hexahydro-2,6-methano-3-benzazocine (I) utilized therein was replaced by an equivalent amount of the corresponding (−)-isomer (prepared according to the procedure of Example 40 of U.S. Pat. No. 4,016,167). The title product was obtained in 82% yield as an oil (~93% purity) of a double bond (cis/trans)isomeric mixture which was used directly in the next step without determining rotation.

(b) (−)-11α-Carbethoxymethyl-6-carbomethoxy-8-methoxy-3-methyl-1,2,3,4,5,6-hexahydro-2,6-methano-3-benzazocine [(−)-III]

The product of step (a) was treated according to the procedure of Example 1, step (b), to obtain the title compound, mp 107°–108° C., $[\alpha]_D^{22}$ −44.8°; $[\alpha]_{365}^{22}$ −191° (c 1.0, methanol).

Anal. calc'd for $C_{20}H_{27}NO_5$: C, 66.46; H, 7.53; N, 3.88. Found: C, 65.94; H, 7.42; N, 3.71; $H_2O$, 0.53.

(c) (−)-11α-(2′-Hydroxyethyl)-6-hydroxymethyl-8-methoxy-3-methyl-1,2,3,4,5,6-hexahydro-2,6-methano-3-benzazocine [(−)-IV]

The product [(−)-III] of step (b) was treated according to the procedure of Example 1, step (c), to obtain the title product in 87% yield, mp 185°–188° C., $[\alpha]_D^{22}$ −57.7°; $[\alpha]_{365}^{22}$ −259° (c 1.15, chloroform).

Anal. calc'd for $C_{17}H_{25}NO_3$: C, 70.07; H, 8.65; N, 4.81. Found: C, 70.20; H, 8.86; N, 4.63.

(d) (−)-3-Methoxy-17-methyl-6-oxamorphinan [(−)-V]

The product [(−)-IV] of step (c) was treated according to the procedure of Example 1, step (d), [only four hours of heating was required] to give the title product in 89% yield. It was isolated as a hydrogen maleate salt from ethyl acetate-acetone, mp 156°–159° C., $[\alpha]_D^{22}$ −18.2°; $[\alpha]_{365}^{22}$ −102.3° (c 1.04, methanol).

Anal. Calc'd for $C_{17}H_{23}NO_2 \cdot C_4H_4O_4$: C, 64.76; H, 6.99; N, 3.60. Found: C, 64.39; H, 6.91; N, 3.46.

EXAMPLE 7

(-)-3-Methoxy-6-oxamorphinan [(-)-VIII]

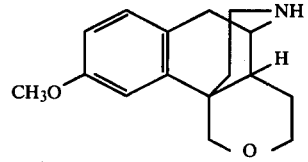

The general procedure of Example 3 was repeated except that the 3-methoxy-17-methyl-6-oxamorphinan (V) utilized herein was replaced by an equimolar amount of the corresponding (−)-isomer [prepared in Example 6, above], to produce the title compound. It was isolated as (+)-hydrogen tartrate from methanol, mp 252°–262° C. (decomp), $[\alpha]_D^{22}$ 0°; $[\alpha]_{365}^{22}$ −41.6° (c 1.17; water).

Anal. calc'd for $C_{16}H_{21}NO_2 \cdot C_4H_6O_6$: C, 64.65; H, 7.23; N, 4.19. Found: C, 63.69; H, 6.96; N, 4.03; $H_2O$, 1.07.

EXAMPLE 8

(−)-17-Cyclopropylmethyl-3-hydroxy-6-oxamorphinan [8 (−)-XI]

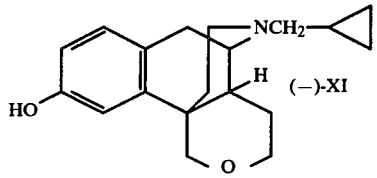

(−)-XI (a) (−)-17-Cyclopropylmethyl-3-methoxy-6-oxamorphinan [(−)-X]

The general procedure of Example 4, step (a) was repeated except that the 3-methoxy-6-oxamorphinan (VIII) utilized therein was replaced by an equimolar amount of the corresponding (−) isomer [prepared in Example 7 above], to produce the title compound. It was isolated as a crystalline (−)-hydrogen tartrate hemimethanolate from methanol, mp 190°–192° C., $[\alpha]_D^{22} -49.5°$; $[\alpha]_{365}^{22} -178°$ (c 1.02, water).

Anal. Calc'd for $C_{20}H_{27}NO_2 \cdot C_4H_6O_6 \cdot \frac{1}{2}(CH_4O)$: C, 61.36; H, 7.36; N, 2.92. Found: C, 61.03; H, 7.39; N, 2.77.

(b) (−)-17-Cyclopropylmethyl-3-hydroxy-6-oxamorphinan [(−)-XI]

The priduct [(−)-X] of step (a) was demethylated by the general procedure of Example 2 to produce the title product. It was purified as a crystalline (−)-tertrate hemihydrate from methanol water, mp 243°–249° C. (decomp), $[\alpha]_D^{22} -61.1°$, $[\alpha]_{365}^{22} -229°$ (c 1.13, water).

Anal. calc'd for $(C_{19}H_{25}NO_2)_2 \cdot C_4H_6O_6 \cdot \frac{1}{2}(H_2O)$: C, 66.55; H, 7.58; N, 3.70; $H_2O$, 1.17. Found: C, 66.47; H, 7.55; N, 3.64; $H_2O$, 1.26.

EXAMPLE 9

3-Acetoxy-17-cyclopropylmethyl-6-oxamorphinan (XV)

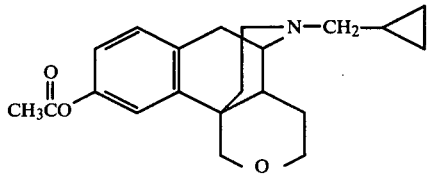

XV

Equimolar quantities of 17-cyclopropylmethyl-3-hydroxy-6-oxamorphinan (XI), acetyl chloride and pyridine are mixed together in dry methylene chloride and the resultant mixture is heated at reflux for several hours to produce the title compound.

EXAMPLE 10

17-Cyclopropylmethyl-3-nicotinoyloxy-6-oxamorphinan (XVI)

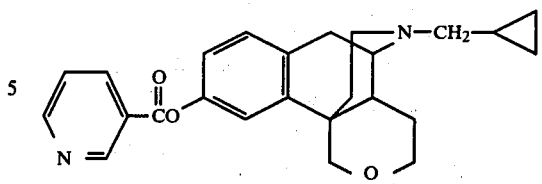

XVI

Equimolar amounts of 17-cyclopropylmethyl-3-hydroxy-6-oxamorphinan (XI), nicotinoyl chloride hydrochloride and pyridine are mixed together in dry methylene chloride and the mixture is heated at reflux for 3 hours to produce the title compound.

EXAMPLE 11

17-Allyl-3-hydroxy-6-oxamorphinan (XVIII)

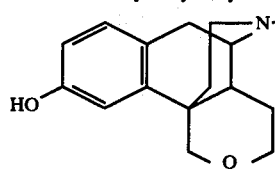

XVIII (a) 17-Allyl-3-methoxy-6-oxamorphinan (XVII)

A mixture of 3-methoxy-6-oxamorphinan (VIII) (0.005 m), allyl bromide (0.006 m) and potassium carbonate (2 g) in 20 ml acetonitrile is heated at reflux for 18 hours. The mixture is filtered and the filtrate concentrated. The residue is treated with water and extracted with ethyl acetate. The extracts are dried ($Na_2SO_4$) and concentrated to give the title compound.

(b) 17-Allyl-3-hydroxy-6-oxamorphinan (XVIII)

The product (XVII) of step (a) is demethylated by the general procedure of Example 2 to produce the title product.

EXAMPLE 12

17-(3′,3′-Dimethylallyl)-3-hydroxy-6-oxamorphinan (XX)

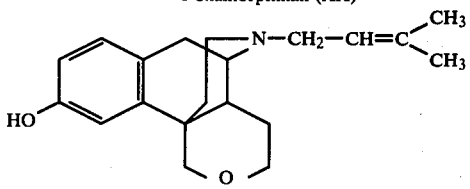

XX

The general procedure of Example 11, Steps (a) and (b), is repeated, except that the allyl bromide utilized therein is replaced by an equimolar amount of 3,3-dimethylallyl bromide, and the title compound is thereby produced.

EXAMPLE 13

3-Ethoxy-6-oxamorphinan (XXX)

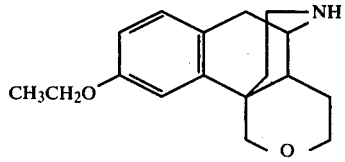

XXX

(a) 3-Acetoxy-17-methyl-6-oxamorphinan (XXVI)

A mixture of the product (VI) of Example 3 (free base) (0.01 m) and 20 ml acetic anhydride is heated at 100° C. for 2 hours. The excess acetic anhydride is removed at reduced pressure. The residue is treated with dilute sodium carbonate and extracted with methylene chloride to produce the title compound.

(b) 3-Acetoxy-17-carbophenoxy-6-oxamorphinan (XXVII)

A mixture of XXVI (0.01 m) from Step (a) above, 4 g potassium carbonate and phenylchloroformate (0.03 m) in 50 ml toluene is heated at reflux for 24 hours. The cooled reaction mixture is treated with water. The toluene layer is separated, dried (MgSO4), filtered and concentrated to give the title product as a crude oil used directly in the next reaction.

(c) 17-Carbophenoxy-3-hydroxy-6-oxamorphinan (XXVIII)

A cooled solution of XXVII from Step (b) above (0.01 m) in 25 ml 2-propanol (~10° C.) is treated with a solution of potassium hydroxide (3 g) in 25 ml water and is stirred under nitrogen at 10° C. for 2 hours. The reaction mixture is acidified with phosphoric acid and the 2-propanol removed at reduced pressure. The aqueous mixture is extracted with methylene chloride. The extracts are dried (MgSO4) and concentrated to produce the title compound.

(d) 17-Carbophenoxy-3-ethoxy-6-oxamorphinan (XXIX)

A mixture of XXVIII (0.005 m) from Step (c) above, ethyl iodide (0.01 m) and potassium carbonate (2 g) in 20 ml acetonitrile is heated at reflux for 18 hours. The mixture is filtered and the filtrate concentrated. The residue is treated with water and extracted with methylene chloride. The extracts are dried (MgSO4), filtered and concentrated to give the title compound.

(e) 3-Ethoxy-6-oxamorphinan (XXX)

A mixture of XXIX (0.005 m) from Step (d) above, 6 g potassium hydroxide, 75 ml 2-propanol and 20 ml water is heated at reflux for 40 hours. The 2-propanol is removed at reduced pressure. The resultant mixture is extracted with methylene chloride. The extracts are dried (Na2SO4), filtered and concentrated to produce the title compound.

EXAMPLE 14

17-Cyclopropylmethyl-3-ethoxy-6-oxamorphinan (XXXIV)

(a) 3-Hydroxy-6-oxamorphinan (XXXI)

3-Methoxy-6-oxamorphinan (VIII) is demethylated using sodium thioethoxide in dimethylformamide by the general procedure of Example 2 to produce the title product.

(b) 17-Cyclopropylcarbonyl-3-hydroxy-6-oxamorphinan (XXXII)

The product XXXI of Step (a) (0.005 m) and triethylamine (1.5 ml) in methylene chloride (30 ml) is treated with a solution of cyclopropylcarbonyl chloride (0.0055 m) in methylene chloride (5 ml). After stirring for 2 hours the mixture is treated with dilute hydrochloric acid. The layers are separated, the methylene chloride layer is washed with water, and the aqueous layers are extracted with two more portions of methylene chloride. The combined methylene chloride layers are dried (MgSO4), filtered and concentrated to give the title product.

(c) 17-Cyclopropylcarbonyl-3-ethoxy-6-oxamorphinan (XXXIII)

A mixture of the product of Step (b) (XXXII) (0.005 m), ethyl iodide (0.006 m) and potassium carbonate (2 g) in 20 ml of acetonitrile is heated at reflux for 18 hours. The mixture is then filtered and the filtrate is concentrated. The residue is treated with water and extracted with ethyl acetate. The extracts are dried (Na2SO4) and concentrated to give the title product.

(d) 17-Cyclopropylmethyl-3-ethoxy-6-oxamorphinan (XXXIV)

The product of Step (c) (XXXIII) (0.005 m) in tetrahydrofuran (20 ml) is added to a suspension of lithium aluminum hydride (0.57 g) in tetrahydrofuran (20 ml), and the mixture is heated at reflux for 18 hours. The mixture is then cooled and saturated sodium sulfate solution (1.8 ml) and a few drops of dilute sodium hydroxide are cautiously added. The mixture is warmed until the solids are completely white. Solid sodium sulfate is added, the solids are removed by filtration and washed well with ethyl acetate. Concentration of the combined filtrate and washes gives the title product.

We claim:

1. A 6-oxamorphinan of the formula

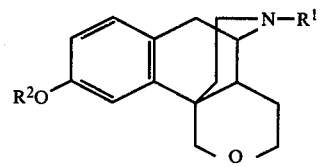

wherein $R^1$ is hydrogen, (lower)alkyl, cyclopropylmethyl, cyclobutylmethyl, allyl, —CH2C≡C—$R^3$,

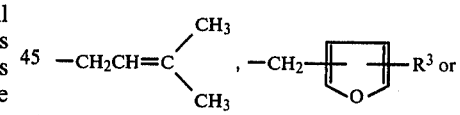

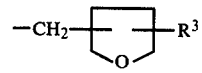

in which $R^3$ is hydrogen or methyl, and $R^2$ is hydrogen, (lower)alkyl, (lower)alkanoyl or nicotinoyl, or a pharmaceutically acceptable salt thereof.

2. A 6-oxamorphinan of claim 1 in which $R^1$ is hydrogen, (lower)alkyl, cyclopropylmethyl or cyclobutylmethyl, and $R^2$ is hydrogen of (lower)alkyl, or a pharmaceutically acceptable salt thereof.

3. A 6-oxamorphinan of claim 1 in which $R^1$ is hydrogen, methyl, cyclopropylmethyl or cyclobutylmethyl, and $R^2$ is hydrogen or methyl, or a pharmaceutically acceptable salt thereof.

4. A 6-oxamorphinan of claim 1 in which $R^1$ is cyclopropylmethyl and $R^2$ is hydrogen or methyl, or a pharmaceutically acceptable salt thereof.

5. A 6-oxamorphinan of claim 1 in which $R^1$ is cyclobutylmethyl and $R^2$ is hydrogen or methyl, or a pharmaceutically acceptable salt thereof.

6. The compound of claim 1 in which $R^1$ is cyclobutylmethyl and $R^2$ is hydrogen, or a pharmaceutically acceptable salt thereof.

7. The (−)-isomer of the compound of claim 6, or a pharmaceutically acceptable salt thereof.

8. The compound of claim 1 in which $R^1$ is cyclopropylmethyl and $R^2$ is methyl, or a pharmaceutically acceptable salt thereof.

9. The (−)-isomer of the compound of claim 8, or a pharmaceutically acceptable salt thereof.

10. 17-Cyclopropylmethyl-3-hydroxy-6-oxamorphinan, or a pharmaceutically acceptable salt thereof.

11. (−)-17-Cyclopropylmethyl-3-hydroxy-6-oxamorphinan.

12. A pharmaceutically acceptable salt of (−)-17-cyclopropylmethyl-3-hydroxy-6-oxamorphinan.

13. (−)-17-Cyclopropylmethyl-3-hydroxy-6-oxamorphinan tartrate.

* * * * *

UNITED STATES PATENT AND TRADEMARK OFFICE
CERTIFICATE OF CORRECTION

PATENT NO. : 4,154,932           PAGE 1 of 3
DATED       : May 15, 1979
INVENTOR(S) : Thomas A. Montzka, John D. Matiskella and Richard A. Partyka It is certified that error appears in the above–identified patent and that said Letters Patent are hereby corrected as shown below:

In column 1, at line 10, Formula XXXV should be shown as:

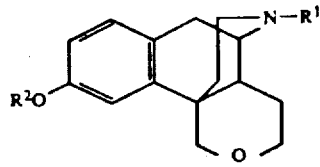

In column 3, at line 47, Formula XXXV should be shown as:

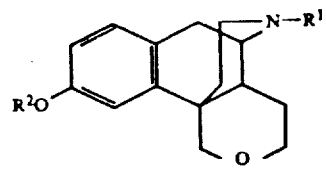

In column 5, at about line 40, Formula III should be shown as:

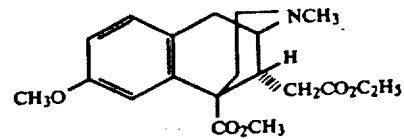

III

UNITED STATES PATENT AND TRADEMARK OFFICE
CERTIFICATE OF CORRECTION

PATENT NO. : 4,154,932
DATED : May 15, 1979
INVENTOR(S) : Thomas A. Montzka, John D. Matiskella and Richard A. Partyka It is certified that error appears in the above-identified patent and that said Letters Patent are hereby corrected as shown below:

In column 6, at about line 40, Formula IV should be shown as:

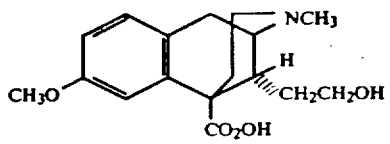

IV

In column 9, at about line 40, Formula (-)-III should be shown as:

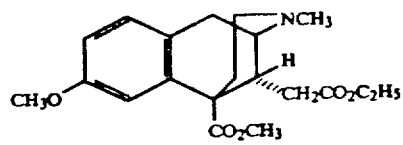

(-)-III

UNITED STATES PATENT AND TRADEMARK OFFICE
CERTIFICATE OF CORRECTION

PATENT NO. : 4,154,932  PAGE 3 of 3
DATED     : May 15, 1979
INVENTOR(S) : Thomas A. Montzka, John D. Matiskella and Richard A. Partyka It is certified that error appears in the above-identified patent and that said Letters Patent are hereby corrected as shown below:

In column 10, at about line 40, Formula (-)-IV should be shown as:

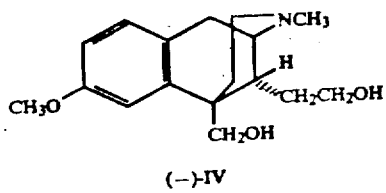

(-)-IV

In column 11, at line 22, Formula XXXV should be shown as:

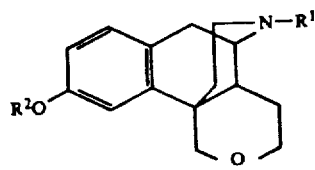

Signed and Sealed this

Second Day of October 1979

[SEAL]

Attest:

RUTH C. MASON
Attesting Officer

LUTRELLE F. PARKER
Acting Commissioner of Patents and Trademarks